(12) United States Patent
Hernandez et al.

(10) Patent No.: US 11,768,117 B1
(45) Date of Patent: Sep. 26, 2023

(54) FIBER LIGHT RELAY SYSTEM WITH QUICK-CONNECT FIBER ANCHOR

(71) Applicant: The Government of the United States of America, as represented by the Secretary of Homeland Security, Washington, DC (US)

(72) Inventors: David Hernandez, Springfield, MO (US); Karmen Noel Lappo, Albuquerque, NM (US); Steven Wayne Bayley, Bosque Farms, NM (US); Mark R. Nissen, Georgetown, TX (US); Cole Sandin, Albuquerque, NM (US); Allen Dean Gorby, Tijeras, NM (US)

( * ) Notice: Subject to any disclaimer, the term of this patent is extended or adjusted under 35 U.S.C. 154(b) by 0 days.

(21) Appl. No.: 18/105,137

(22) Filed: Feb. 2, 2023

Related U.S. Application Data

(60) Provisional application No. 63/393,383, filed on Jul. 29, 2022.

(51) Int. Cl.
*G01N 33/22* (2006.01)
*G01L 5/14* (2006.01)

(52) U.S. Cl.
CPC .............. *G01L 5/14* (2013.01); *G01N 33/227* (2013.01)

(58) Field of Classification Search
CPC ................................ G01L 5/15; G01N 33/227
See application file for complete search history.

(56) References Cited

U.S. PATENT DOCUMENTS

| | | | | |
|---|---|---|---|---|
| 5,477,156 | A * | 12/1995 | Uher | G01P 15/12 324/715 |
| 5,828,797 | A * | 10/1998 | Minott | F01D 21/003 385/115 |
| 6,320,184 | B1 * | 11/2001 | Winklhofer | F02B 77/08 250/554 |
| 6,667,801 | B1 * | 12/2003 | Dubaniewicz | F41A 31/00 356/256 |
| 9,664,622 | B2 * | 5/2017 | Vannas | G01J 5/05 |
| 2002/0134138 | A1 * | 9/2002 | Philipp | G01J 5/0893 73/35.07 |

(Continued)

OTHER PUBLICATIONS

Lappo, Karmen N., et al., "Fiber Light Relay System (FLRS) in Non-Ideal Granular Explosives for Shock Front Monitoring", SAND2018-7354C (2018).

*Primary Examiner* — Alexander A Mercado
(74) *Attorney, Agent, or Firm* — Lavanya Ratnam; Robert W. Busby; Kelly G. Hyndman

(57) ABSTRACT

An apparatus for forming an anchor to connect a fiber to an explosive charge wall includes an anchor insert tab disposed on the interior side of the wall, a top plate disposed on the exterior side of the wall, an ST connector disposed on the exterior side and attached to the top plate to position the ST connector at the fiber insert wall opening for receiving the fiber, a plurality of zip ties extending through the anchor insert tab, the wall, and the top plate, and a plurality of locking members one for each of the zip ties. The zip ties each have a locking head disposed on the interior side of the wall to press the anchor insert tab against the interior wall surface. The locking members are engaged with the zip ties to press the top plate against the exterior wall surface to form the anchor.

27 Claims, 16 Drawing Sheets

(56) References Cited

U.S. PATENT DOCUMENTS

| | | | |
|---|---|---|---|
| 2015/0153285 A1* | 6/2015 | Vannas | G01J 5/0818 |
| | | | 250/227.11 |
| 2015/0268041 A1* | 9/2015 | Scheid | F42B 35/00 |
| | | | 73/35.17 |
| 2015/0268216 A1* | 9/2015 | Chavez | G01N 21/17 |
| | | | 422/82.11 |
| 2018/0348021 A1* | 12/2018 | Ziems | G01D 11/26 |
| 2021/0131835 A1* | 5/2021 | Daoud | G01D 5/35312 |
| 2022/0319291 A1* | 10/2022 | Dittmer | G01J 5/041 |

* cited by examiner

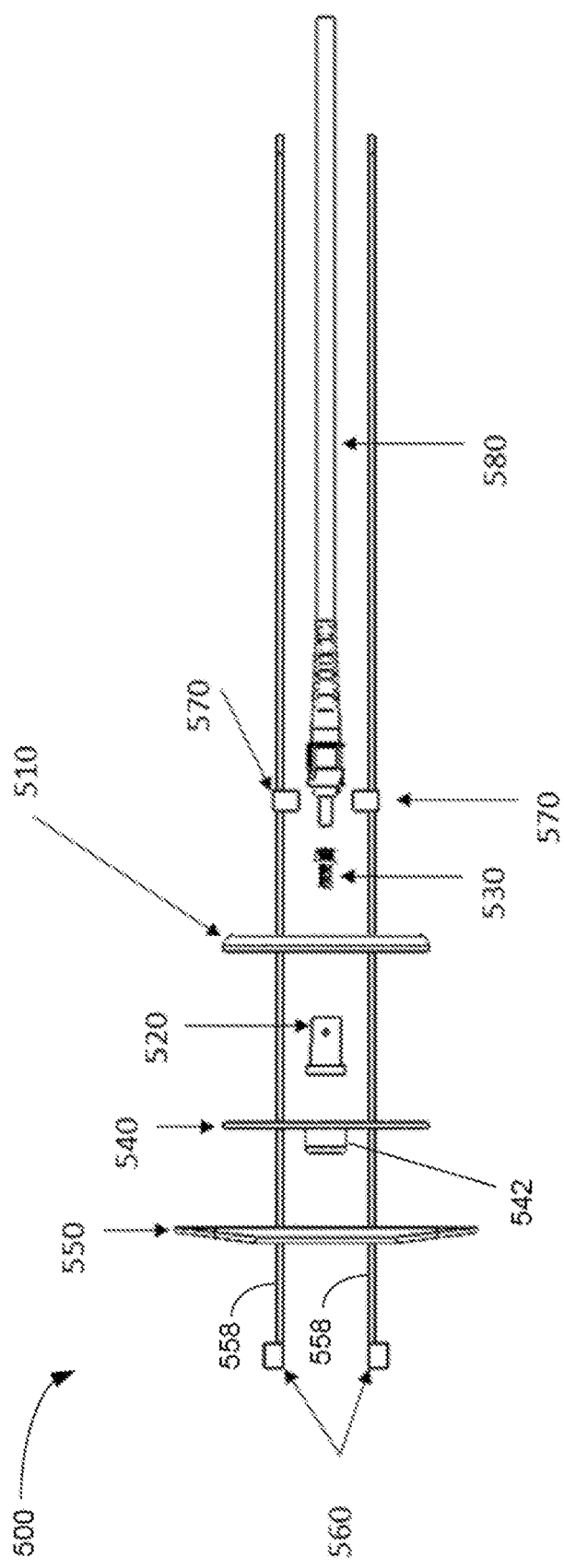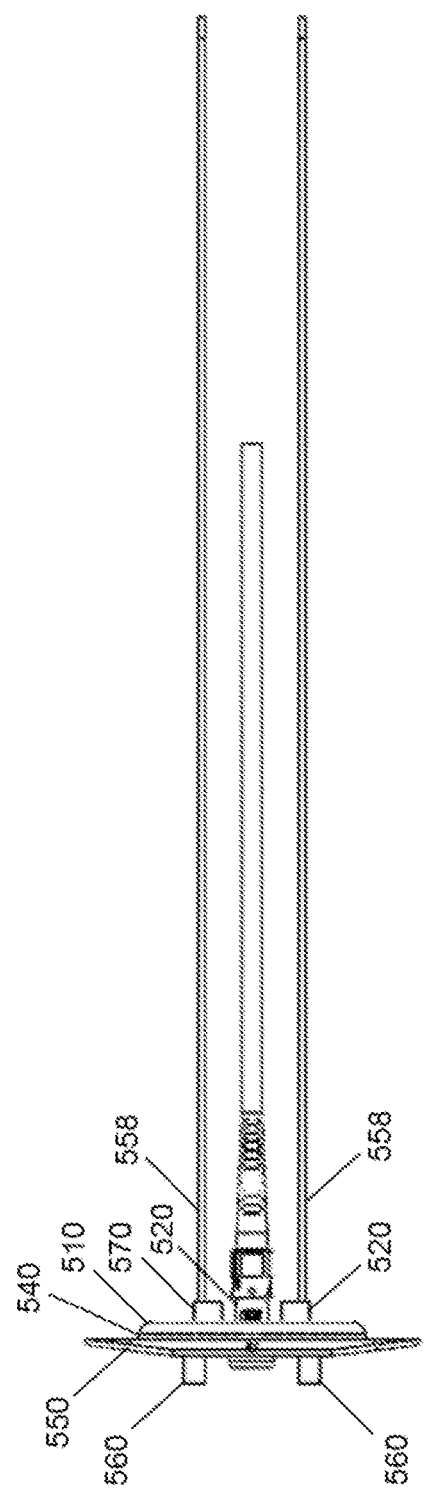
FIG. 5A
FIG. 5B (B)

710

(A)

Table 1. Instrumentation Velocity Measurements.

| Instrument | Velocity (mm/μs) | Deviation |
|---|---|---|
| CVP 1 | 3.51 | |
| FLRS 1 | 3.54 | 0.9% |
| TOA 2 | 3.51 | |
| CVP 2 | 3.42 | |
| FLRS 2 | 3.39 | 1.0% (CVP) 3.6% (TOA) |

FIG. 10

FIBER LIGHT RELAY SYSTEM WITH QUICK-CONNECT FIBER ANCHOR

CROSS-REFERENCE TO RELATED APPLICATIONS

The application is a nonprovisional of and claims the benefit of priority from U.S. Provisional Patent Application No. 63/393,383, filed on Jul. 29, 2022, entitled FIBER LIGHT RELAY SYSTEM WITH QUICK-CONNECT FIBER ANCHOR, the entire disclosure of which is incorporated herein by reference.

SUMMARY STATEMENT OF GOVERNMENT INTEREST

The present invention was made with support from the United States Department of Homeland Security (DHS) under contract 70RSAT20KPM000063 and by an employee of DHS in the performance of their official duties. The U.S. Government has certain rights in this invention.

FIELD

The discussion below relates generally to explosives testing and, more particularly, to a Fiber Light Relay System (FLRS) and method in non-ideal granular explosives for shock front monitoring.

BACKGROUND

To understand the reactive front behavior in non-ideal granular or heterogeneous blended explosive formulations, in-situ shock position measurements are desired. While traditional techniques such as flash x-ray, embedded electromagnetic or pressure gauges, and timing pins are practical in a lab or small-scale experiments, design they become logistically challenging, cost prohibitive, or technically inappropriate to deploy as the experimental size grows (e.g., 100 lbs. or greater).

SUMMARY

Monitoring detonation shock front in large explosive charge geometries can become expensive and at times cost prohibitive. Traditional methods require sensors/probes/fibers, signal conditioning, data acquisition equipment, channel per location/probe, etc. Hundreds of channels equate to many scopes and can become cost prohibitive. Past efforts missed critical data due to cost limitations.

Embodiments of the present invention are directed to a way to preserve appropriate spatial and temporal resolution while reducing cost. Tools and methods are developed for a more efficient and defensible characterization of large-scale charges. These tools and methods can reduce equipment and labor and maintain sample location count.

In recent experiments, measuring the shock front position and shape was desired through the length of columnar and rectangular charges. The FLRS was developed as a cost-effective way to collect shock front time-of-arrival over one or several spatial planes during a single experiment. With the appropriate resolution point cloud, the individual and time grouped points can then be resolved to calculate shock velocity and wave front shape relative to position and time respectively. The individual and time grouped points can then be resolved to calculate shock velocity and shape relative to position and time respectively.

To determine the validity of using the FLRS to monitor the shock front in granular non-ideal explosives, the system was deployed experimentally in parallel with traditional instrumentation techniques on the same explosive charge. Piezoelectric pins and a continuous velocity probe were used as the baseline time of shock arrival and velocity measurement techniques respectively. FLRS parameters, fiber end preparation, and output light signal focusing lenses were varied to determine the impact on the recorded fiber optical output.

Embodiments of the invention use optical fibers to relay the shock front light through a patch panel to a high-speed video camera. The camera can observe output of 10 s-100 s of fibers without additional data acquisition hardware. Software resolves fiber light output as a function of time from the high-speed video. Fiber locations and light arrival are used to calculate detonation shock transit properties.

Python software developed in house automated the detection of each fiber output within the high-speed video footage. The local area is identified and shown on a user interface as a circle surrounding the area being monitored and spot identification number. The localized area pixels light intensity is tabulated in an output file with respect to the video frame. The user is provided control to specify the light intensity threshold to identify and the data output file is automatically generated to utilize in data correlation. The software automatically identifies the maximum light for each spot and respective time within the video it occurs. The data is later combined with location details enabling the calculations of velocity between points on the charge.

An aspect of the invention is directed to an apparatus for forming an anchor to connect a fiber to an explosive charge wall having an interior wall surface on an interior side and an exterior wall surface on an exterior side, and a fiber insert wall opening through the wall between the interior wall surface and the exterior wall surface. The apparatus comprises: an anchor insert tab disposed on the interior side of the wall; a top plate disposed on the exterior side of the wall; an ST connector disposed on the exterior side of the wall, the ST connector being attached to the top plate to position the ST connector at the fiber insert wall opening for receiving the fiber; a plurality of zip ties extending through the anchor insert tab, the wall, and the top plate, the zip ties each having a locking head disposed on the interior side of the wall to press the anchor insert tab against the interior wall surface; and a plurality of locking members one for each of the plurality of zip ties, the locking members being disposed on the exterior side of the wall and engaged with the zip ties to press the top plate against the exterior wall surface to form the anchor.

In some embodiments, the locking members comprise locking heads of additional zip ties. An explosive charge wall may include a plurality of anchors each formed by the above-described apparatus, at a plurality of locations on the wall, for connecting a plurality of fibers to the wall.

Another aspect of the invention is directed to a method of forming an anchor to connect a fiber to an explosive charge wall having an interior wall surface on an interior side and an exterior wall surface on an exterior side, and a fiber insert wall opening through the wall between the interior wall surface and the exterior wall surface. The method comprises: placing an anchor insert tab on the interior side of the wall over the fiber insert wall opening; attaching an ST connector to a top plate; placing the top plate on the exterior side of the wall to position the ST connector at the fiber insert wall opening for receiving the fiber; extending a plurality of zip ties through the anchor insert tab, the wall, and the top plate, the zip ties each having a locking head disposed on the interior side of the wall to press the anchor insert tab against the interior wall surface; and sliding a plurality of locking members on the exterior side of the wall, one for each of the plurality of zip ties, to engage with the zip ties to press the top plate against the exterior wall surface to form the anchor.

In some embodiments, the interior side of the wall is a fill side of the wall. The method further comprises cutting a longitudinal slit in the wall at a location of the fiber insert wall opening and inserting the anchor insert tab through the longitudinal slit from the exterior side into the interior side of the wall to be positioned over the fiber insert wall opening on the fill side. The method may further include removing locking heads of additional zip ties to be used as the locking members.

The method may be used to form a plurality of anchors at a plurality of locations on the wall, which includes, at each of the plurality of locations: placing a corresponding anchor insert tab on the interior side of the wall over a corresponding fiber insert wall opening; attaching a corresponding ST connector to a corresponding top plate; placing the corresponding top plate on the exterior side of the wall, to position the corresponding ST connector at the corresponding fiber insert wall opening for receiving a corresponding fiber; extending a plurality of corresponding zip ties each through the corresponding anchor insert tab, the wall, and the corresponding top plate, the corresponding zip ties each having a corresponding locking head disposed on the interior side of the wall to press the corresponding anchor insert tab against the interior wall surface; and sliding a plurality of corresponding locking members on the exterior side of the wall, one for each of the plurality of the corresponding zip ties, to engage with the corresponding zip ties to press the corresponding top plate against the exterior wall surface.

In specific embodiments, the method may further comprise forming the plurality of anchors at the plurality of locations on the wall, before connecting the fiber to the ST connector at any of the anchors. A plurality of fibers having ST-terminated fiber input ends and fiber output ends may be connected between the wall to receive the ST-terminated fiber input ends and a fiber panel configured to receive and align the fiber output ends toward a camera. The method may further comprise presetting the locations on the wall to position the ST-terminated fiber input ends of the plurality of fibers and presetting locations on the fiber panel to position the fiber output ends of the plurality of fibers, before connecting the plurality of fibers between the wall and the fiber panel. The method may further comprises labeling the plurality of fibers according to the preset locations of the wall for connecting the fiber input ends and the preset locations on the fiber panel for connecting the fiber output ends, before connecting the plurality of fibers between the wall and the fiber panel.

Another aspect of the invention is directed to an apparatus for forming an anchor to connect a fiber to an explosive charge wall having an interior wall surface on an interior side and an exterior wall surface on an exterior side, and a fiber insert wall opening through the wall between the interior wall surface and the exterior wall surface. The apparatus comprises: an anchor insert tab disposed on the interior side of the wall; an ST connector disposed on the exterior side of the wall for receiving the fiber; a top alignment plate disposed on the exterior side of the wall between the exterior wall surface and the ST connector, the top alignment plate including a bushing configured to extend through the fiber insert wall opening and to receive the ST connector to align the ST connector with the fiber insert wall opening for receiving and aligning the fiber; a plurality of zip ties extending through the anchor insert tab, the wall, and the top alignment plate, the zip ties each having a locking head disposed on the interior side of the wall to press the anchor insert tab against the interior wall surface; and a plurality of locking members one for each of the plurality of zip ties, the locking members being disposed on the exterior side of the wall and engaged with the zip ties to press the top alignment plate against the exterior wall surface to form the anchor.

In specific embodiments, an explosive charge wall has a plurality of anchors each formed by the apparatus described above, at a plurality of locations on the explosive charge wall, for connecting a plurality of fibers to the explosive charge wall at a plurality of fiber insert wall openings. The interior side is a fill side of the explosive charge wall. The explosive charge wall may include a plurality of longitudinal slits at the plurality of locations at which the plurality of anchors are formed each by inserting the anchor insert tab through the corresponding longitudinal slit from the exterior side into the interior side of the explosive charge wall to be positioned over the corresponding fiber insert wall opening on the fill side.

In accordance with another aspect, a system for explosive testing system comprises: an explosive charge having an explosive charge wall; a fiber panel; a plurality of fibers connected between the explosive charge wall and the fiber panel; and a plurality of devices each for forming an anchor to connect a fiber of the plurality of fibers to the explosive charge wall having an interior wall surface on an interior side and an exterior wall surface on an exterior side, and a fiber insert wall opening through the wall between the interior wall surface and the exterior wall surface. Each device includes an anchor insert tab disposed on the interior side of the wall; a top plate disposed on the exterior side of the wall; an ST connector disposed on the exterior side of the wall, the ST connector being attached to the top plate to position the ST connector at the fiber insert wall opening for receiving the fiber; a plurality of zip ties extending through the anchor insert tab, the wall, and the top plate, the zip ties each having a locking head disposed on the interior side of the wall to press the anchor insert tab against the interior wall surface; and a plurality of locking members one for each of the plurality of zip ties, the locking members being disposed on the exterior side of the wall and engaged with the zip ties to press the top plate against the exterior wall surface to form the anchor.

In accordance with another aspect, a method for explosive testing comprises: connecting fiber output ends of a plurality of fibers to a fiber panel; and forming a plurality of anchors at a plurality of anchor locations on an explosive charge wall of an explosive charge to receive fiber input ends of the plurality of fibers, the explosive charge wall having an interior wall surface on an interior side and an exterior wall surface on an exterior side, and a plurality of fiber insert wall openings through the explosive charge wall between the interior wall surface and the exterior wall surface at the plurality of anchor locations for the plurality of anchors. Forming an anchor of the plurality of anchors comprises placing an anchor insert tab on the interior side of the wall over the fiber insert wall opening; attaching an ST connector to a top plate; placing the top plate on the exterior side of the wall to position the ST connector at the fiber insert wall opening for receiving the fiber; extending a plurality of zip ties through the anchor insert tab, the wall, and the top plate, the zip ties each having a locking head disposed on the interior side of the wall to press the anchor insert tab against the interior wall surface; and sliding a plurality of locking members on the exterior side of the wall, one for each of the plurality of zip ties, to engage with the zip ties to press the top plate against the exterior wall surface to form the anchor.

Other features and aspects of various examples and embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

FIG. 5A shows an exploded view of a "quick connect" fiber anchor.

FIG. 5B shows a fully assembled "quick connect" fiber anchor.

FIG. 10 shows Table 1 presenting experimental results of instrumentation velocity measurements.

DETAILED DESCRIPTION

A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

Experimental Setup

The FLRS has been developed as a cost-effective way to collect shock front time-of-arrival over one or several spatial planes during a single experiment. The individual and time grouped points can then be resolved to calculate shock velocity and shape relative to position and time respectively.

Current hydrocodes are well developed for equilibrium explosive behavior predictions. These are explosives that almost instantaneously transition from reactants (explosive molecule) to products (gasses, water vapor, and metal oxides). These models can be used for non-ideal explosives but with much less confidence. To develop a model for a granular non-ideal explosive, it is desired to monitor both shock velocity and wave curvature to better tune the model to replicate the shock performance in time with higher confidence within the parameters tested.

Figure 1:
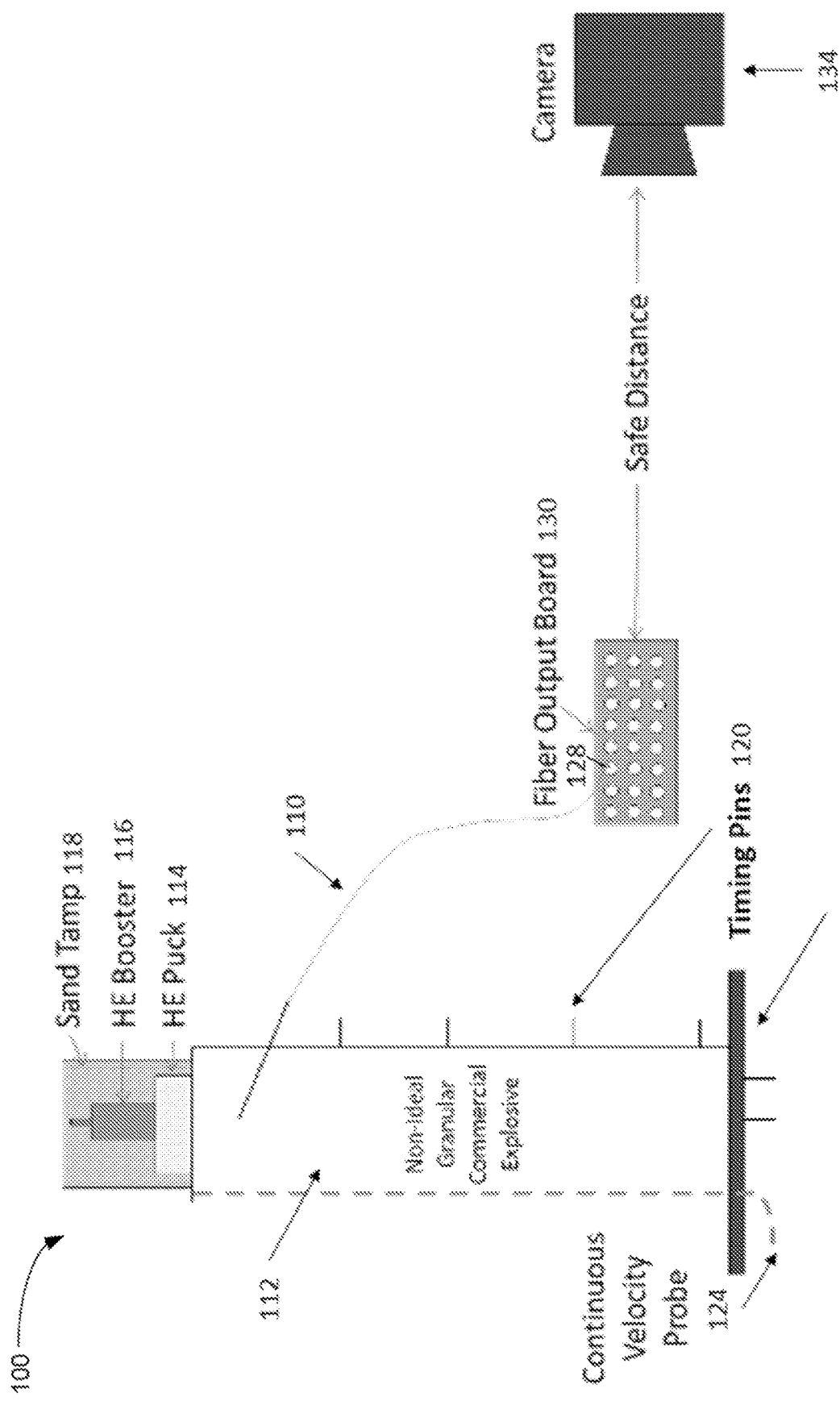
FIG. 1 is an overall schematic view of an experimental setup (not to scale) of a Fiber Light Relay System (FLRS) according to an embodiment of the invention.

FIG. 1 is an overall schematic view of an experimental setup (not to scale) of a Fiber Light Relay System (FLRS) according to an embodiment of the invention. The FLRS 100 includes an explosive charge with optical fibers 110 (e.g., 1 mm PMMA (polymethyl methacrylate) fibers) embedded in the charge column 112 at known heights and internal radii from the charge centerline or at the explosive charge wall interface. A HE puck 114 is a hand packed short cylinder of plasticized bulk explosive. A HE booster 116 may be a commercial PETN pressed cylinder booster that surrounds the detonator improving the total pressure and surface area of shock pressure to the HE puck 114. A sand tamp filler 118 behind the HE booster 116 and HE puck 114 to improve energy transfer into the Non-Granular Commercial Explosive fill by minimizing explosive products venting into the air. Timing pins 120 are piezoelectric (PZT) time of arrival (TOA) pins used as a comparison method for monitoring shock time of arrival as it travels down the side wall of the explosive fill. A continuous velocity probe 124 is used in a method in the commercial blasting industry to continuously monitor the shock location and velocity through and explosive column along a single line. An instrumented witness plate 122 also contained timing pins 120 and optical fibers 110 to monitor the shock time of arrival at the base of the charge.

The output end 128 of each fiber 110 is routed to an output panel or manifold panel 130 that aligns the fibers toward a high-speed camera 134 (higher than 50,000 FPS). The PMMA fiber 110 imbedded in non-ideal granular explosive charge may be routed to the manifold panel 130 with a grid of collimating lenses. Each fiber 110 may be mapped from its position in the charge to a specific lens on the manifold 130. The high-speed camera 134 monitors the lens output from a pre-determined distance. The video captured shows the many points on the manifold. Each point is resolved as several pixels in the video and monitored for light intensity with respect to time. The time resolution is translated into time of shock arrival at the respective locations in the charge. This data is analyzed to determine shock position spatially in the charge and shock velocity is calculated between the points.

Figure 2:
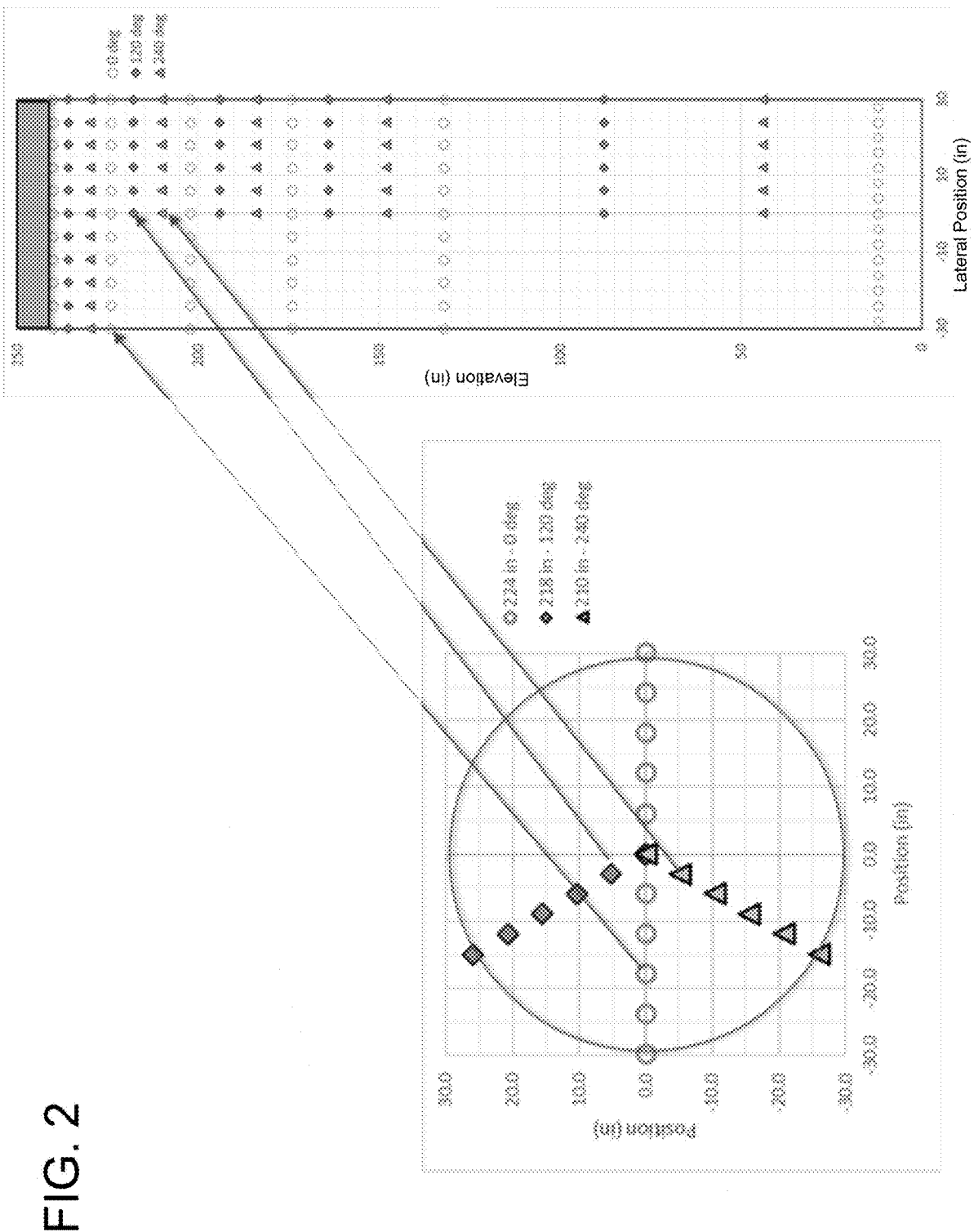
FIG. 2 shows an example of a fiber placement.
Figure 2A:
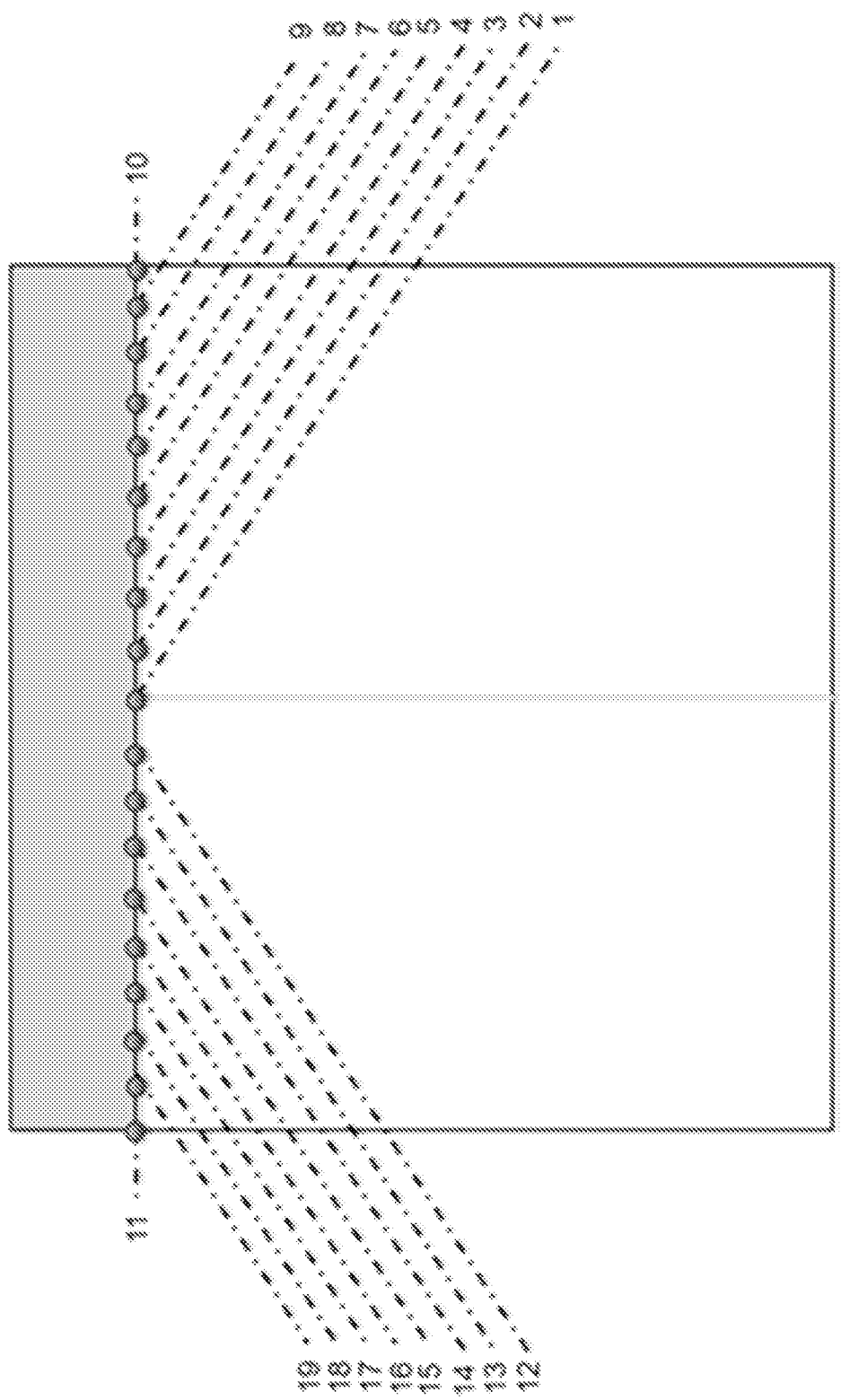
FIG. 2A shows details of the insertion of fibers according to an embodiment.

FIG. 2 shows an example of a fiber placement. The placement of the fibers internal to the charge at across many different planes has been designed to observe the shock propagation over time while minimizing the shock front disturbance by rotationally offsetting the location line for the next collection plane. FIG. 2A shows details of the insertion of fibers according to an embodiment. Along a single line, the respective fibers would be sequentially inserted as shown from the nearest side wall. A line in an additional plane would then be inserted at a pre-determined radial offset from the previously installed line of fibers. The process would continue as desired and can be physically constructed without hardware interference and/or damage.

Additionally, the use of fibers with a small core diameter relative to the charge size will minimize shock disturbance. For example, fibers with a 1 mm core can be used with a charge size of many inches or feet in diameter. For this reason, a method to imbed fibers at known locations within the charge has been developed.

Figure 3:
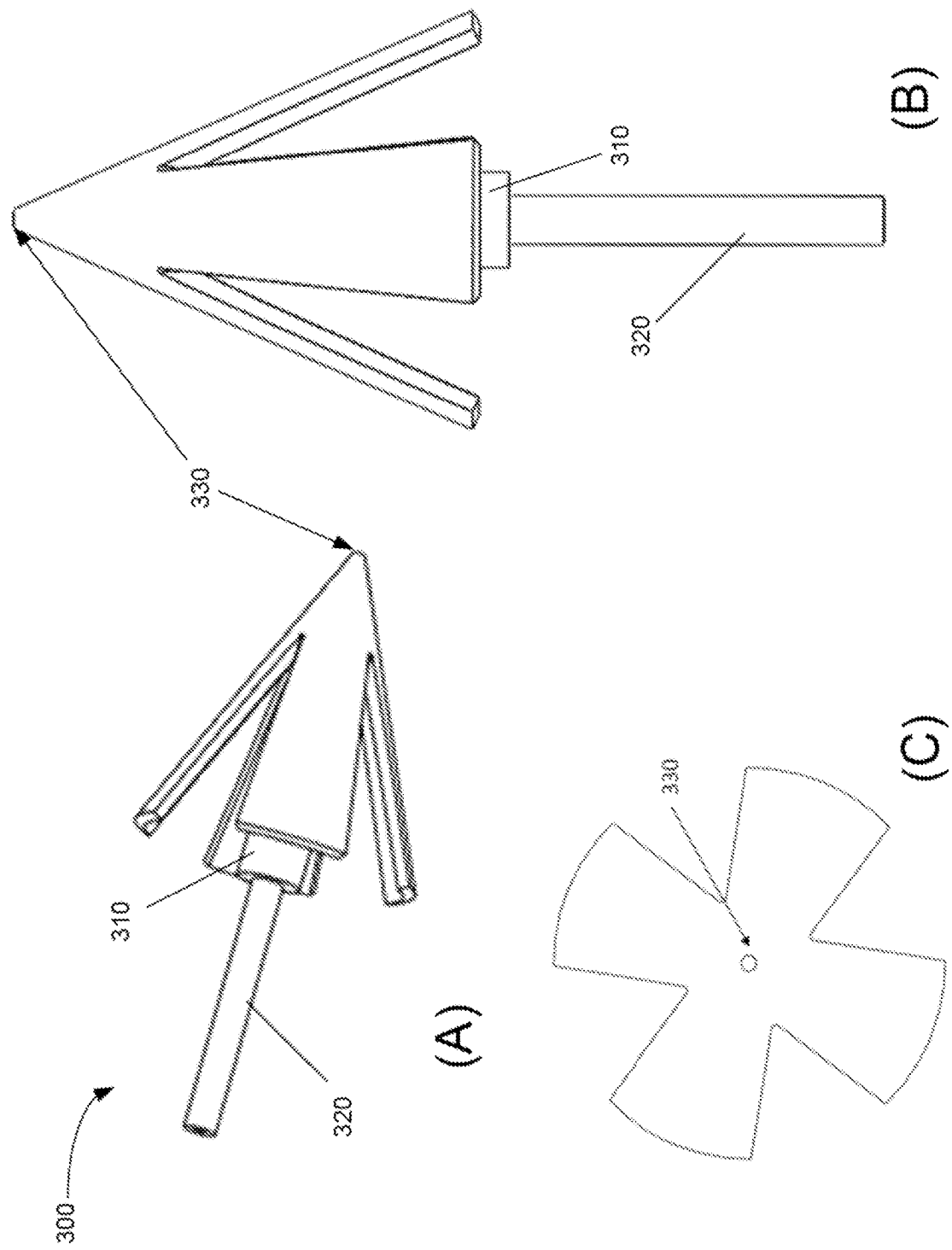
FIG. 3 shows an example of a flexible 3D printed "arrowhead" anchor including (A) a first perspective view, (B) a profile or elevational view, and (C) a head on or plan view.

FIG. 3 shows an example of a flexible 3D printed "arrowhead" anchor 300 including (A) a first perspective view, (B) a profile or elevational view, and (C) a head on or plan view. The arrowhead has a stem 310 with a fiber sleeve 320 extending from a proximal end and an arrowhead tip 330 at a distal end. The fiber is inserted into the fiber sleeve 320 until the polished fiber face of the fiber is flush with the arrowhead anchor tip 330. The anchors 300 may be manually inserted into predrilled hole in the charge container 112. The insertion may be facilitated by use of a round tube "push rod" with the same outer diameter as the stem 310 and an inner diameter that is larger than the sleeve 320. There is a potential danger of breakage to glued fiber during insertion of the arrowhead anchors 300.

The arrowhead fiber anchors 300 are configured to rest just inside a base plate or be pushed into the bulk (e.g., charge column 112 of a granular explosive charge) and then anchored into place at a prescribed angle and distance inserted. The angle prevents the detonation shock front from damaging the fiber before reaching the tip where the light will enter for data collection.

Figure 4:
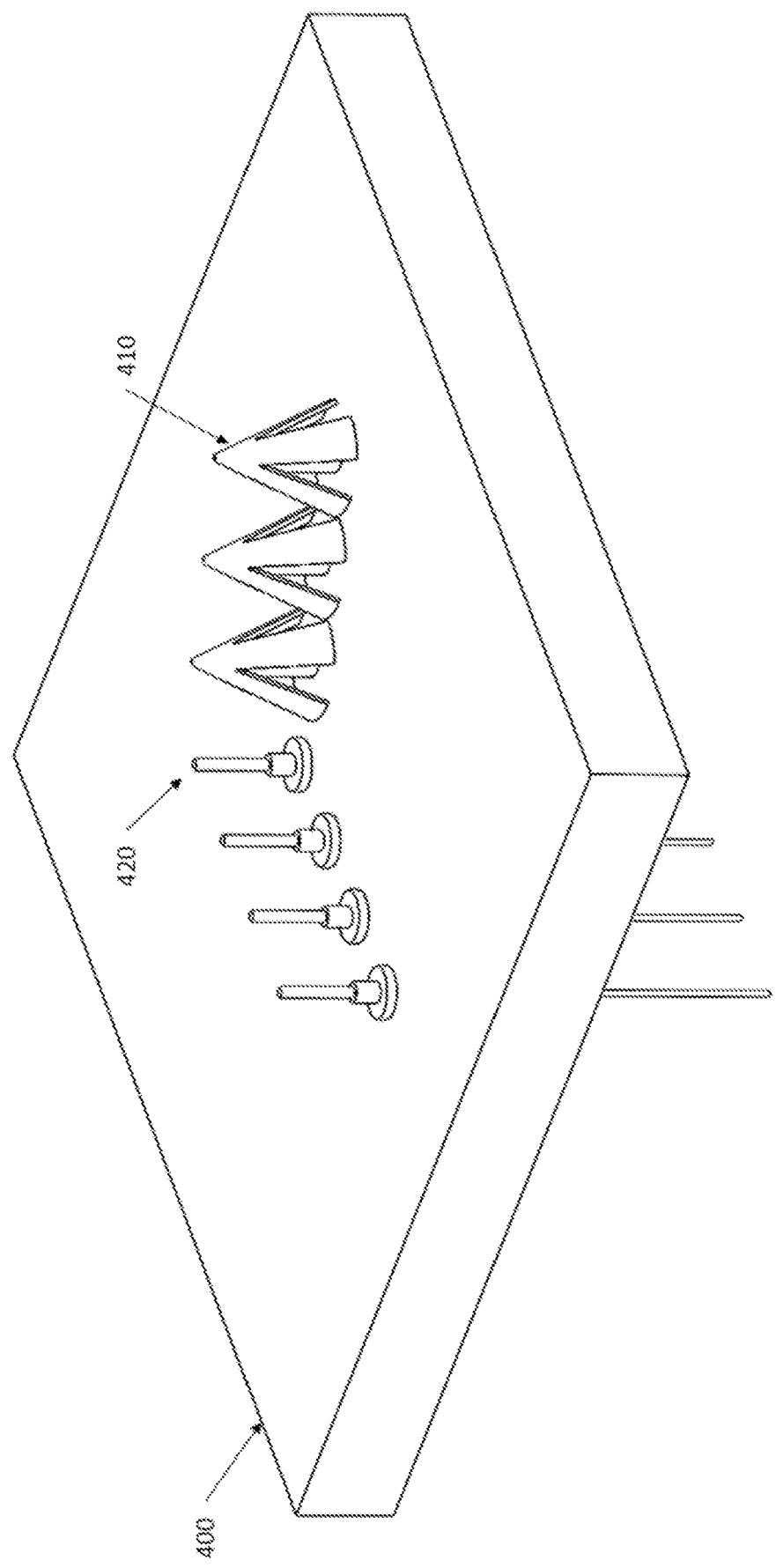
FIG. 4 shows an example of anchoring the fibers just before the shock front reaches a witness plate at the base of a charge.

FIG. 4 shows an example of anchoring the fibers with an arrowhead fiber anchor 410 just before the shock front reaches a witness plate 400 at the base of a charge. Piezoelectric (PZT) time-of-arrival (TOA) pins 420 are also present in this witness plate, offset from the fiber anchors by 60 degrees. The PZT pins were used to compare the FLRS method to known diagnostic techniques.

This anchoring system can be used to accurately define the fiber location. It utilizes the conical arrowhead style mount with 1-mm bore through the center to accept the fiber. The fiber is glued in place flush with the tip of the mount in lab prior to testing. The mount may be 3D printed out of a flexible material or may be manufactured in bulk with different methods.

FIG. 5A shows an exploded view of a "quick connect" zip tie fiber anchor 500 which includes a top plate 510, an ST connector 520, fastening members 530, a top alignment plate 540, an anchor insert tab 550, zip ties 558 with locking heads 560, and locking members 570. The ST connector 520 is attached to the top plate 510 with small #4-40 machine screws 530. The top alignment plate 540 rests outside of the charge surface and the anchor insert tab 550 is inserted into the charge. The top alignment plate 540 includes a bushing 542 configured to extend through a fiber insert wall opening of the charge wall and to receive the ST connector 520 to align the ST connector 520 with the fiber insert wall opening for receiving and aligning the ST-terminated fiber. Zip ties 558 with locking heads 560 are used to secure the assembly to the charge. The separate set of locking members 570 may include another set of locking heads 570, which may be cut off from a separate or additional set of zip ties, that are placed on the assembly zip ties 558 to tighten the assembly. The ST-terminated 1 mm PMMA fiber 580 is connected to the ST connecter 520 after the zip ties 558 are secured. FIG. 5B shows a fully assembled "quick connect" fiber anchor 500 as installed into a charge (see FIGS. 12A and 12B).

The two-piece "quick-connect" zip-tie based design allows the anchor to be installed into the charge without fiber present. The ST connector on a back plate is designed to keep the corresponding fiber at a known standoff controlled by manufacturing tolerances. As such, the anchor may be installed into the charge without fiber present. To locate the fibers, a global coordinate system is generated for the charge assembly. Each probe location is measured and logged with respect to the global system. This enables the later analysis for the full charge functionality to be tracked.

Figure 6A:
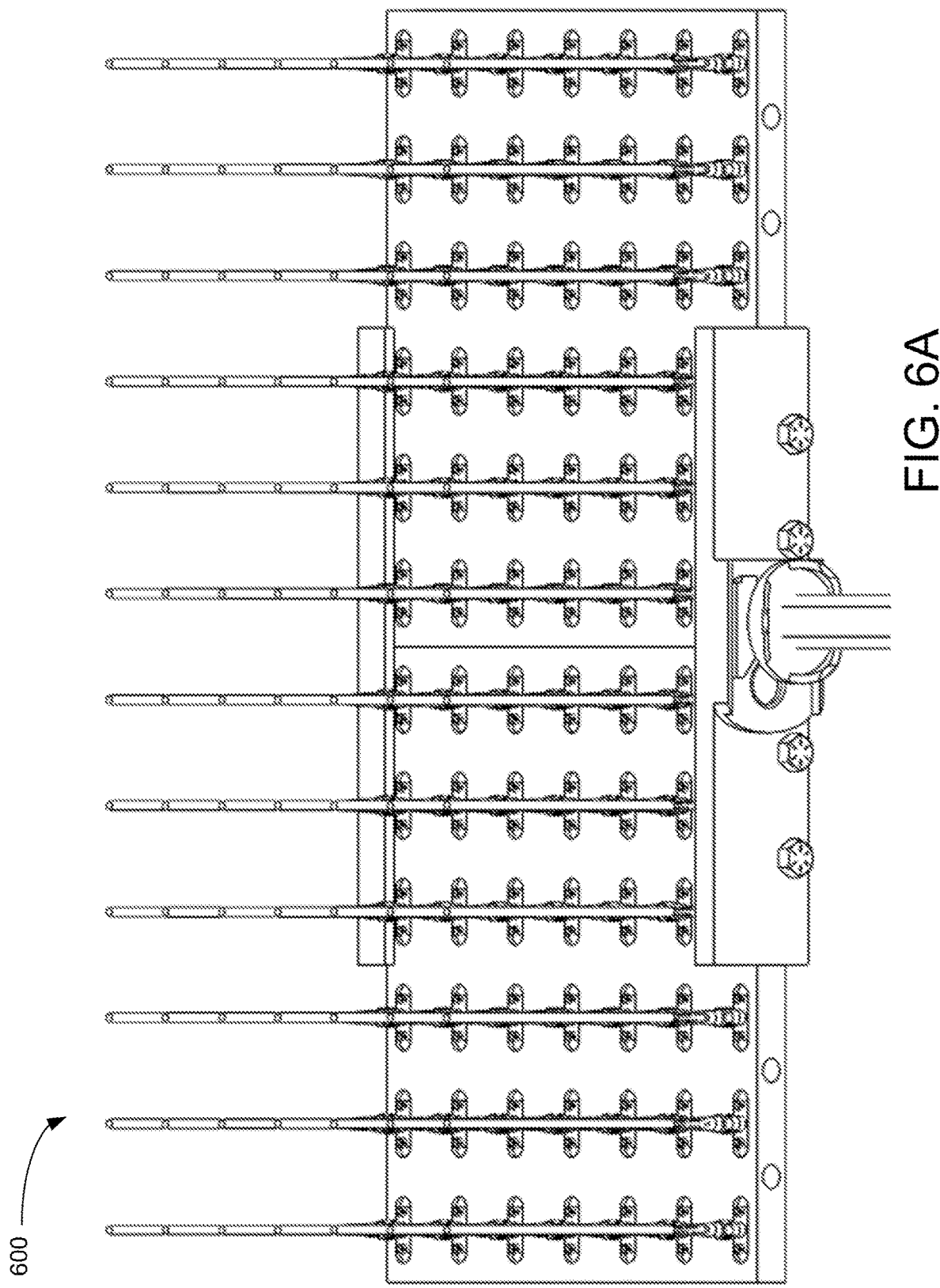
FIG. 6A shows a back/insertion side of an example of a fiber panel.
Figure 6B:
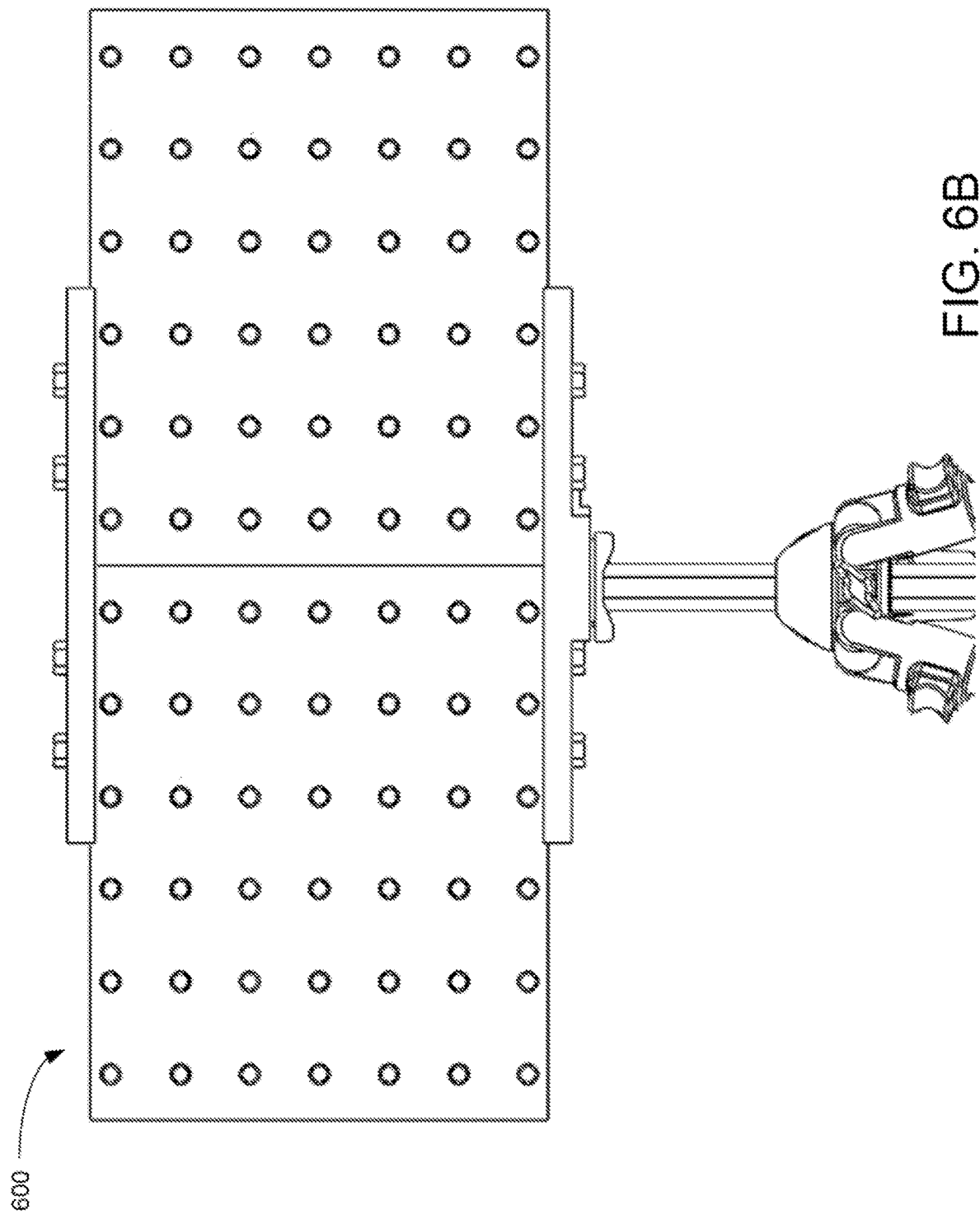
FIG. 6B shows a front/output side of an example of a fiber panel.

FIG. 6A shows a back/insertion side of an example of a fiber panel pair 600. FIG. 6B shows a front/output side of an example of the fiber panel pair 600. The holes in each panel are separated sufficiently to allow each point to be resolved by the camera independently. In the example shown, each panel of the pair of panels 600 includes an array of seven horizontal rows of six (7×6) rectangularly spaced grid of holes with recessed collimating lenses. A through hole in the back of each fiber panel 600 allows for a 1-mm ST-terminated PMMA fiber to be aligned to the lens with the proper standoff. There is a glue mount for the lens and an ST connector for the fiber. The fibers are connected to the back of the manifold and 7×6 arrays of lenses may be installed into each manifold panel.

Any production method/material is permissible. The panels may be machined out of aluminum. One example uses a 3D printed plastic that has good alignment in the build direction. This will keep all the fibers in alignment pointing toward a common point (i.e., the camera). The good co-alignment of fibers should optimize the fiber light reception at the camera for all fibers. For transmission fibers that terminate in glue joints, manifold production requires lead time for production and glue up of fibers and lenses in advance. Glue up of in-hand manifold would take about one day (e.g., 18 man-hours). The use of ST connections provides industry standard quick connections that can be done in the field. Manifold assembly time is reduced from days to minutes. Assembly can be done in the field, protecting the fibers during transport. The manifold improvements described above utilize rapid prototyping and quick connect COTS parts to streamline the installation process, improve alignment, and minimize custom polishing of fiber ends.

Examples of the fiber cable selected for current and past embodiments include 1-mm core diameter unjacketed PMMA fiber with both ends cleaved and 1-mm core jacketed PMMA fiber. ST connectors were provided at both ends of the jacketed fiber. The jacketed fiber could be cut in half to provide two ST-to-cleaved fibers or left as a single unit, depending on charge attachment scheme. If using ST-ST, no field cleaving/polishing of the fiber was necessary and purely COTS items could be used.

ST connectors on the rear of the manifold 600 mitigate the alignment uncertainty of labor-intensive glue joints. The fibers can also be disconnected from the ST connectors and relocated if needed due to installation errors or desired configuration changes.

Figure 6C:
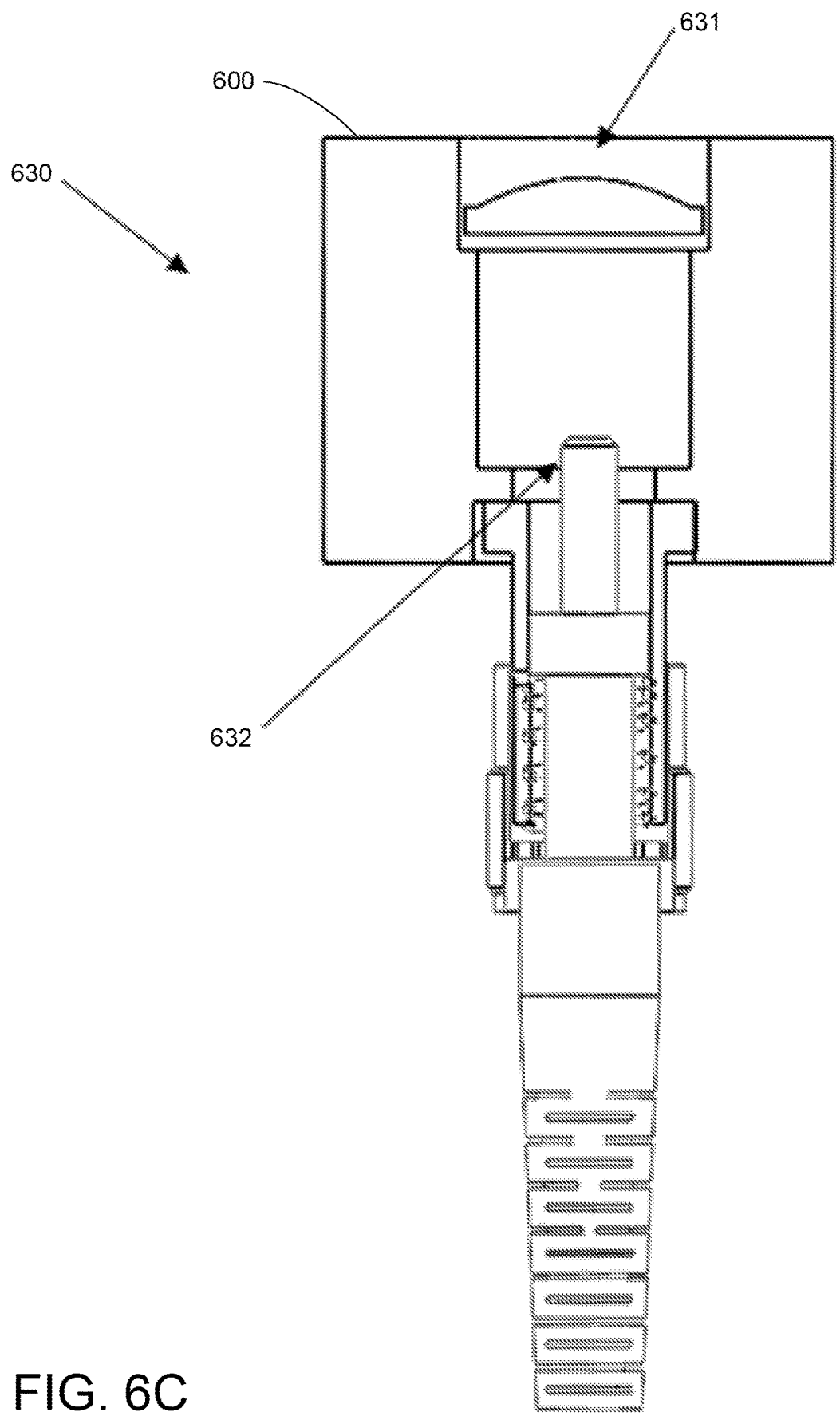
FIG. 6C shows a cross-sectional view of a recessed lens and ST connector mount on a fiber panel.

FIG. 6C is a cross-sectional view illustrating an example of a connection 630 between a fiber and a fiber panel/manifold 600. A recessed plano-convex lens 631 (of the grid of recessed collimating lenses) may be glued into the front of the manifold 600. The proper alignment of the inserted fiber 632 with the lens 631 can be seen.

Furthermore, the top and bottom holders may be custom fabricated to attach to a COTS tripod with a photography head with fine adjustments in all directions. The manifold may include a custom notch that readily slides into the receptor on the tripod and is latched to secure it in place. The photography tripod head allows small, controlled movements to sweep through the camera field of view and obtain the angle that produces the maximum light intensity.

Figure 7:
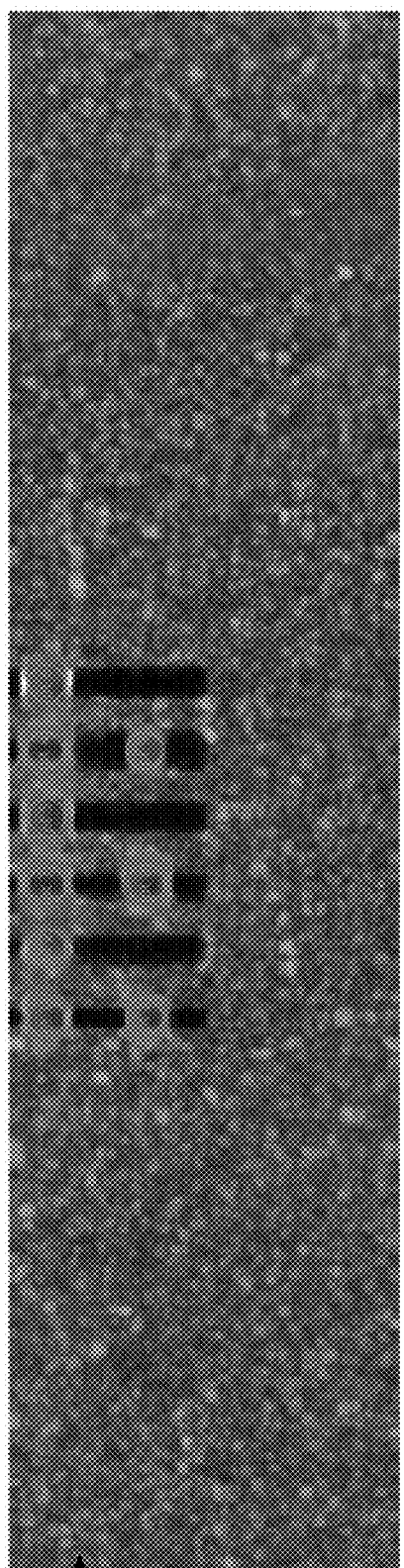
FIG. 7 shows an example of a software analysis solution.
Figure 7:
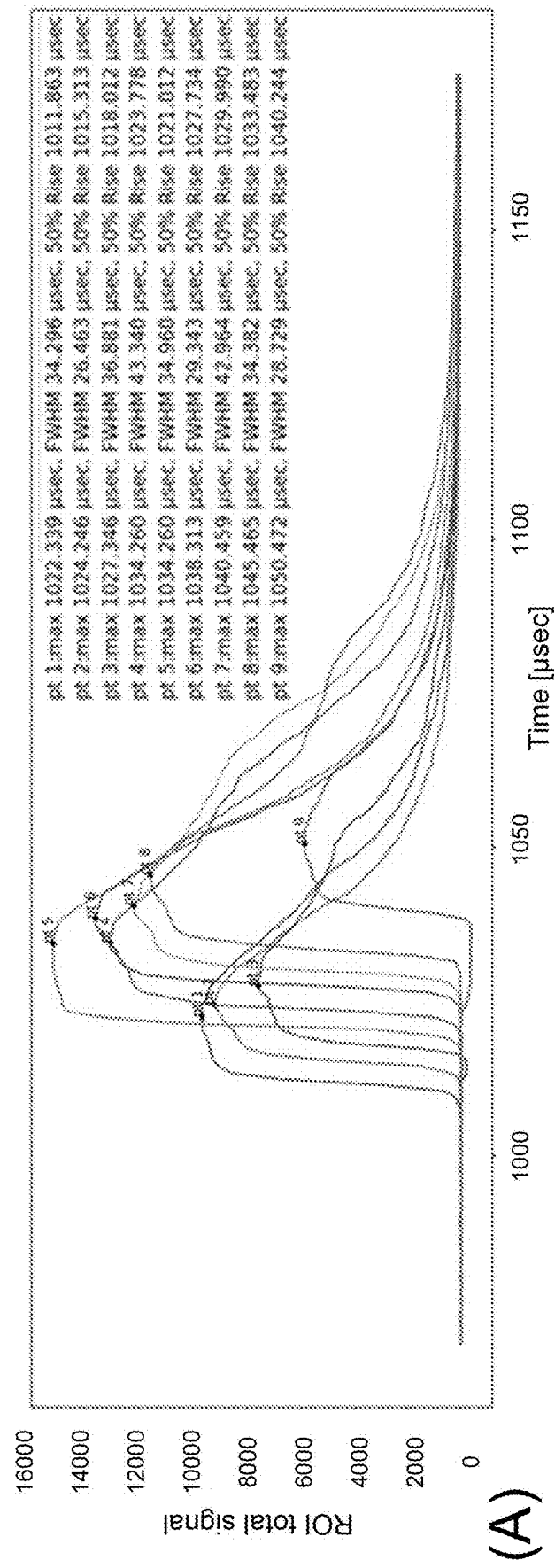

COTS software may be used to track pixel intensity vs. time. Python software has been developed to track fiber output localized average pixel intensity vs. time in user defined regions of interest. FIG. 7 shows an example of the Python software output 700 including (A) a graph of pixel intensity versus time and (B) an image of peak pixel intensities. This software provides an image of all peak pixel intensities 710 "superimposed" above a graph of pixel intensity versus time for each region of interest (ROI). The peak intensities are labeled by order of occurrence. Control over threshold intensities may be given to the user. Output may be in CSV (comma-separated values) or some other format.

Figure 8:
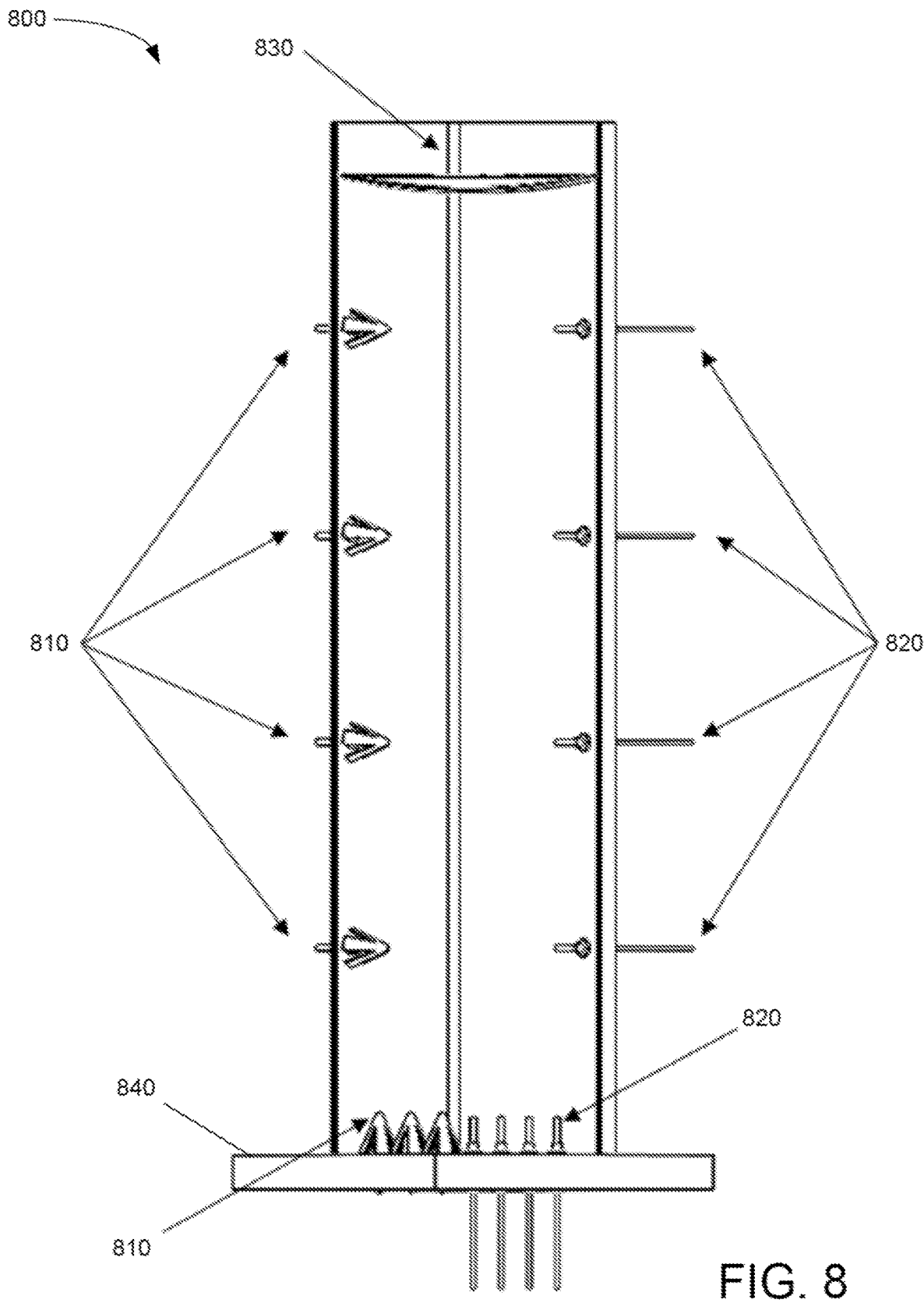
FIG. 8 shows an experimental charge with FLRS, timing pins, and continuous velocity probes installed.

FIG. 8 shows an experimental charge 800 used in a proof-of-concept test with FLRS arrowhead anchors 810, PZT timing pins 820, and continuous velocity probes 830 installed. Continuous velocity probes 830 were aligned along the charge centerline/axis and outside the charge wall aligned with the charge axis. Piezoelectric pins 820 were aligned along the axis wall and along the base plate 840.

All fiber connections in the proof-of-concept test (both charge and manifold end) were glue joints. The traditional anchor method (FIG. 3) was labor intensive and posed the risk of getting glue on the cleaved fiber face, causing an artificial reduction in light collection. Assembly of both anchors and the manifold had to be done in the lab. Transport of manifold with attached fibers risked breakage of fibers. In the present disclosure, ST connections provide industry standard quick connections that can be done in the field (FIGS. 5A & 5B). Manifold assembly time is reduced from days to minutes. Assembly can be done in the field, protecting fibers during transport.

Figure 9:
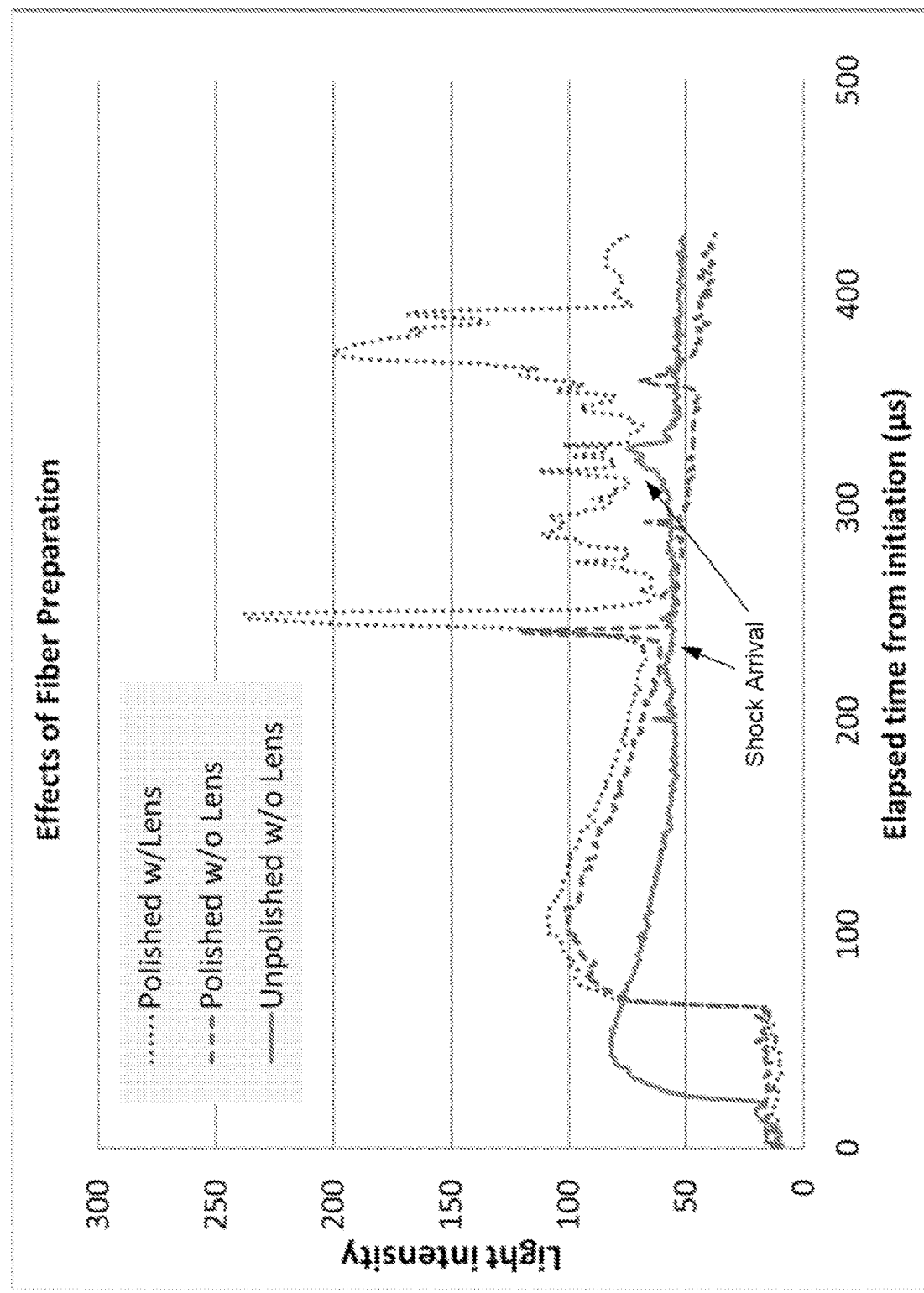
FIG. 9 is a graph of fiber signal versus FLRS parameters illustrating experimental results.

FIG. 9 is a graph of fiber signal versus FLRS parameters illustrating experimental results. The fiber light output intensity was measured relative to time to evaluate the validity of the FLRS technique to detect a shock time-of-arrival in non-ideal granular explosives. The fiber output signal intensity varied greatly depending on the FLRS parameters used. The light intensity with time increased in magnitude as both fiber polishing and focus lenses were added on the manifold end. The signals for cleaved optical fibers without polishing and/or lenses were not distinguishable from the baseline noise in the data traces indicating additional fiber preparation and light focusing to the camera are necessary. The signal rapidly gaining intensity to a level well above the baseline makes the signal easily distinguishable in time. The time-of-arrival for each signal was documented as the peak half height for each fiber signal.

FIG. 10 shows Table 1 presenting experimental results of instrumentation velocity measurements. The inter-sensor shock velocity was calculated from each instrumentation type. The results were compared in Table 1 and resulted in a maximum variance of 3.6% for the FLRS velocity measurement as compared to either the piezoelectric time-of-arrival pins or continuous velocity probes for each test. In the table, data is noted for FLRS, CVP (continuous velocity probe), and TOA (time-of-arrival) pin methods. The CVP is a commercial method that measures the resistance along a thin metal tube probe. As the shock damages and collapses the probe, a resistance change is observed correlating to the remaining length of the tube. TOA pins are used to monitor the voltage across a crystal that becomes increasingly conductive when subjected to increasing shock pressures. When an intense pressure strikes the pin, the resulting voltage spike indicates the shock time of arrival at the pin location. A series of pins can be used to develop a shock arrival and velocity profile over time using the relevant pin location information. Both CVP and TOA pin techniques are demonstrated and trusted methods in the explosive test community and compared to demonstrate that the FLRS is working as intended and comparable to known technologies.

Figure 11:
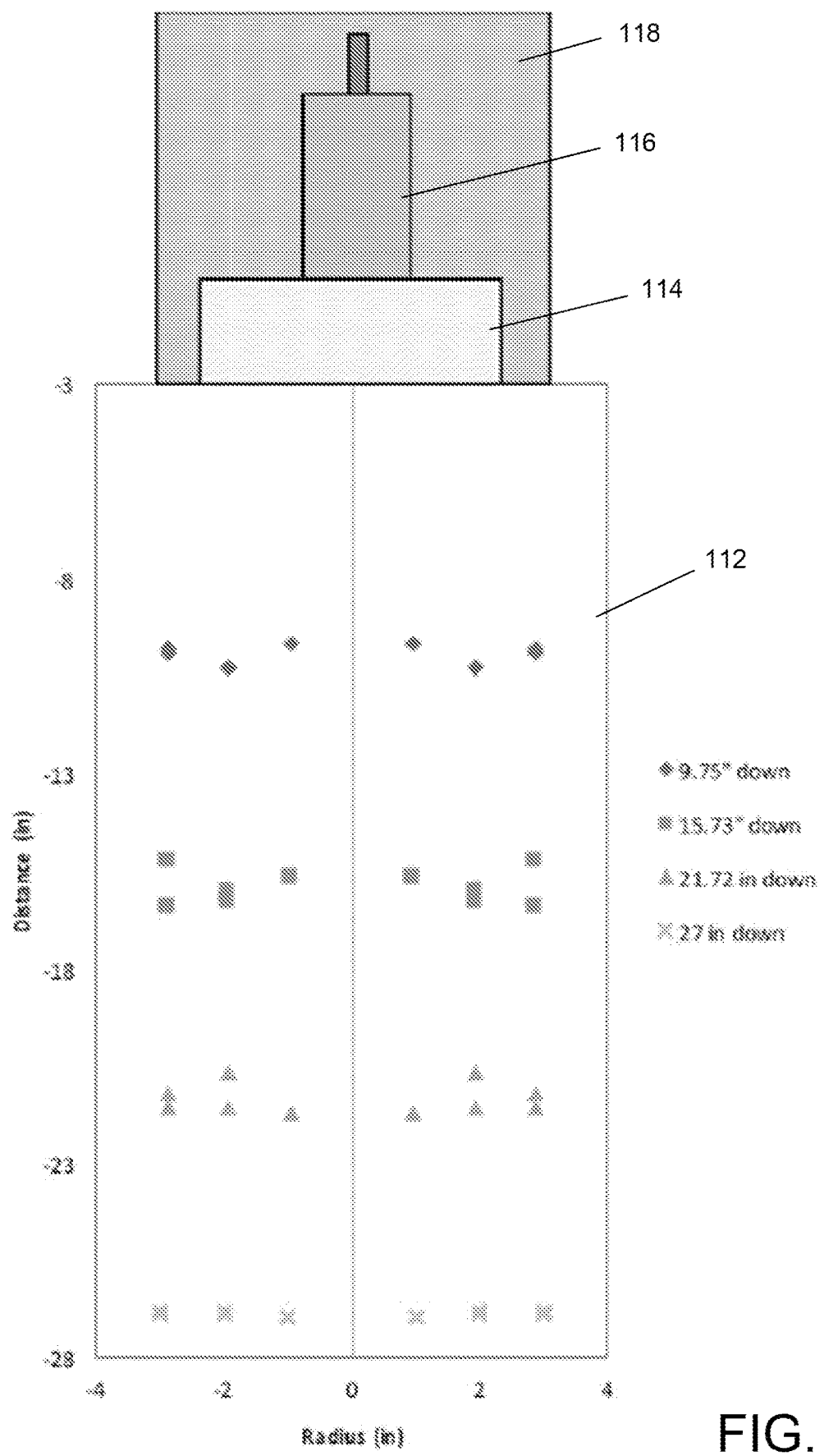
FIG. 11 is a schematic view showing shock positions detected by the FLRS in-situ fibers.

FIG. 11 is a schematic view showing shock positions detected by the FLRS in-situ fibers in the charge column 112. It illustrates the variation in shock arrival time and average inter-sensor shock velocity at a given distance into the charge which was used to approximate the shock position as a function of radius. FIG. 11 shows the estimated shock front profiles at each distance into the charge, with symmetry assumed across the charge axis (centerline of the charge column 112).

It is desired to produce and measure an intense light signal with a rapid rise time to indicate shock arrival. Both ends of the fibers need to be polished and a focusing lens should be used on each fiber to obtain a sufficient signal strength. Without these parameters, the output signal is not sufficiently above the baseline and background light intensity noise levels to confidently differentiate shock arrival.

The small variation in FLRS calculated shock velocity as compared to both the piezoelectric pins and continuous velocity probe measurements confirmed that the FLRS technique is a valid system to monitor the shock position with time. The shock front curvature could be resolved more accurately with increased fiber location resolution at a given distance into the charge. In addition, the fiber tips could be coated with a thin film (e.g., sputter coated or painted with aluminized powder) that illuminates (decomposition is exothermic and light producing) rapidly in a shock environment. This could further increase the signal intensity and therefore confidence in the shock arrival time.

Figure 12A:
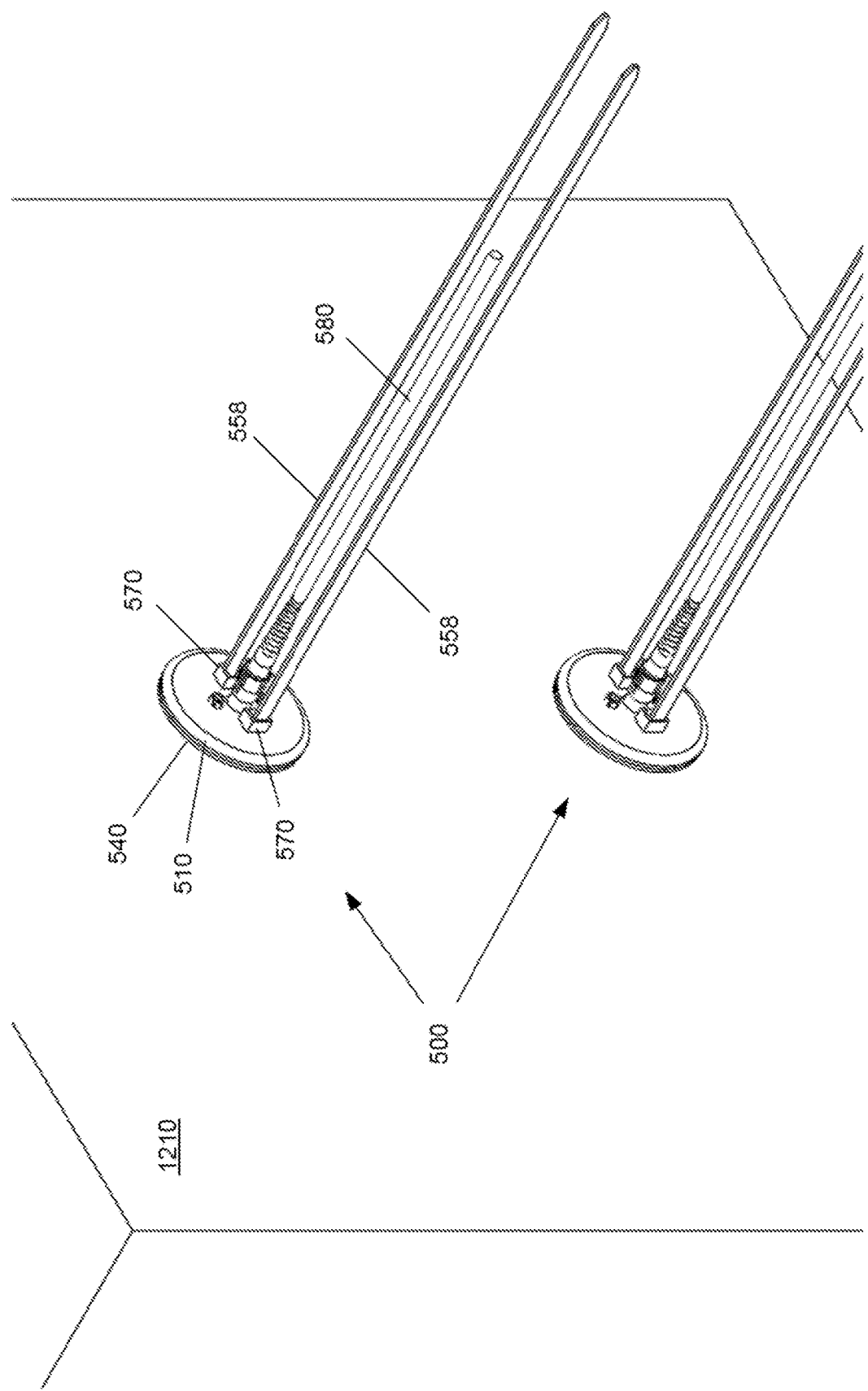
FIG. 12A shows an outside isometric view of a "quick-connect" anchor inserted into a representative charge wall.
Figure 12B:
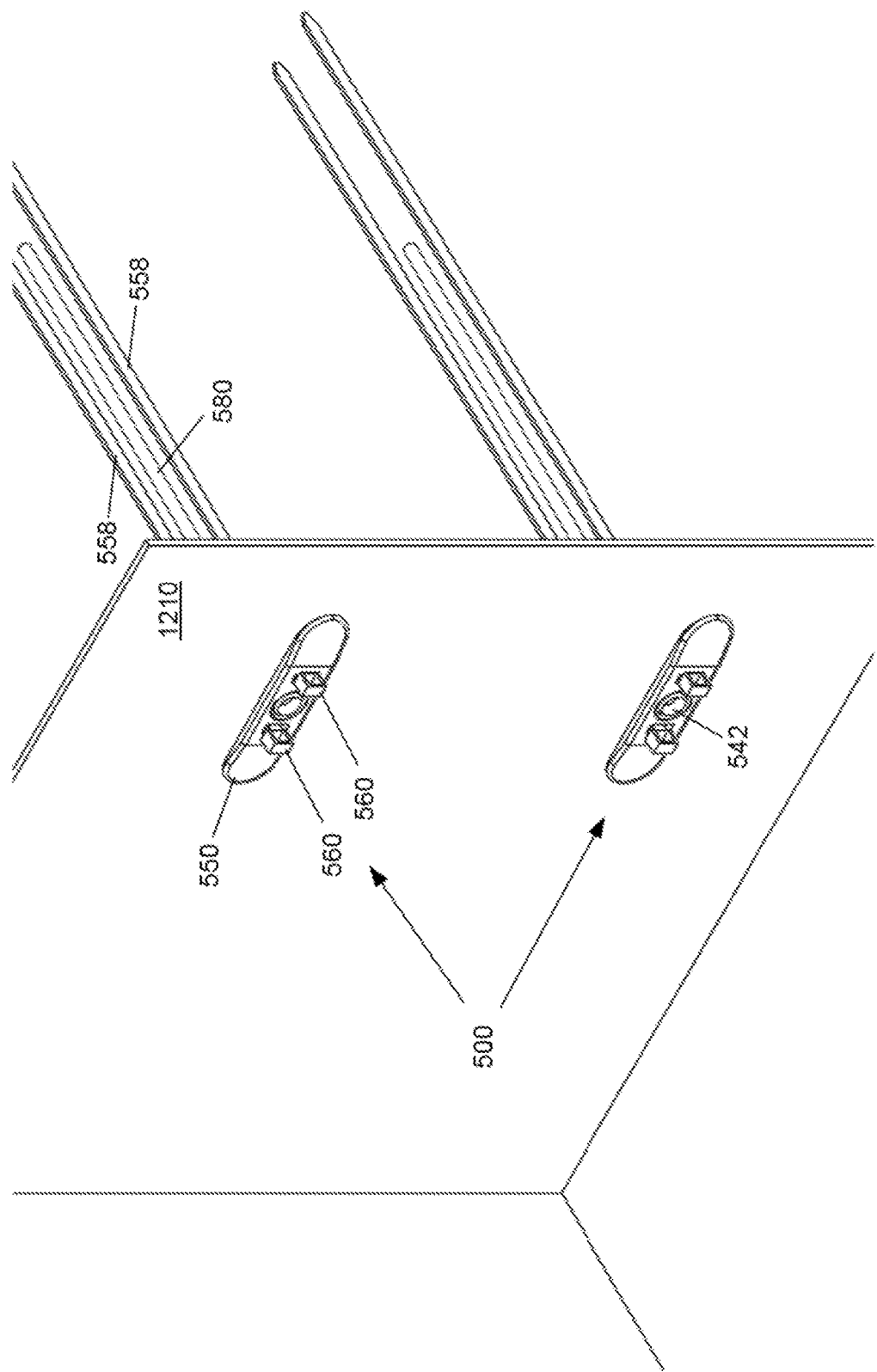
FIG. 12B shows a fill side isometric view of a "quick-connect" anchor inserted into a representative charge wall.

FIG. 12A depicts two "quick-connect" anchors 500 attached to a representative charge wall 1210. The assembly zip ties 558 may be cut after installation is completed. The distance between each anchor 500 can be determined by the technician to fit the needs of the test. FIG. 12B shows a fill-side isometric view of the inserted anchors 500 from inside the charge (i.e., fill side). The anchor insert tab 550 can be seen resting against the inside of the charge wall 1210 on the fill side. The bushing 542 of each top alignment plate 540 extends through the corresponding fiber insert wall opening of the charge wall 1210 to receive the corresponding ST connector 520 to align the ST connector 520 with the corresponding fiber insert wall opening for receiving and aligning the ST-terminated fiber. The locking heads 560 of the assembly zip ties 558 are disposed on the fill-side of the charge wall 1210. On the opposite side, the separate set of locking heads 570 are placed on the assembly zip ties 558 to press the top plate 510 and the top alignment plate 540 against the exterior side of the charge wall 1210 to tighten the assembly. The ST-terminated 1 mm PMMA fiber 580 is connected to the ST connecter 520, which has been attached to the top plate 510, after the assembly is secured to the charge.

One process of installing the quick-connect zip-tie anchor 500 is as follows. (1) Determine and mark the desired anchor point on the charge wall. (2) Place a strip of duct tape over the desired anchor location for rigidity. (3) Using a knife, cut a 2" to 3" long slit horizontally in the charge wall at the marked location. (4) Loosely assemble the quick-connect anchor 500 as shown in FIG. 5A. (5) Insert the anchor insert tab 550 into the charge wall slit. (6) Maneuver the anchor insert tab 550 using the zip ties 558 until the anchor insert tab 550 grabs the charge wall and cannot be easily removed. (7) Using the locking members 570, tighten the components to the charge wall. (8) Connect the ST fiber 580 to the ST connector 520.

There are increasing losses in electrical systems over very long cable lengths. Traditional systems are cable length limited for high frequency measurements and will need heaving structures to protect DAQs (Data Acquisitions) in relatively close proximity to charges.

During test scale increases, this makes the FLRS more efficient in setup and cost effective for tests with 10 s-100 s of probes. Traditional systems would need to be placed increasingly farther away or with more robust structural protection. The FLRS manifold, fibers, and anchors are expendable for each detonation and the camera is located at a safe distance (e.g., up to 800') from test ground zero as needed. The equipment mitigation infrastructure and safe distance to avoid damage are greatly reduced compared to traditional systems. Instead of buying additional DAQs and cables for the number of probes desired, only more manifold panels, fibers, and tripods are used.

For example, the time to set up 45 channels with a traditional system would take days to a week. The FLRS system can be set up the day of the test in less than 6 hours, provided that the communications to the personnel bunker are previously verified, the fibers are pre-bundled/labeled, the system is ready to plug and plan, and the fiber placement has already been planned at preset anchor locations on the charge and respective preset locations on the manifold.

The FLRS reduces the number of interfaces between data acquisition systems to a single camera. This reduces the risk of a dis-synchronization to 0 when a single camera is used. Also, the infrastructure and time to set up and confirm time synchronization are eliminated. This reduction applies to the required number of fibers, redundant recording of trigger on each DAQ, and hours to days of setup and confirmation in traditional techniques.

The cost of several technicians could be $1000/day per tech. Cables and sensors to properly synchronize data could be $100s to $1000s. The improper synchronization of critical data can cost the entire test if necessary data cannot be obtained or is invalid due to lack of synchronization. That could be $10K, $100K, $1M or more based on the cost of test items, infrastructure, planning, and labor.

The manifold is designed to provide optimal alignment of all fibers and lenses, maximizing output light intensity. The lens spacing on the manifold is designed to correlate with rectangular pixel spacing of Phantom highspeed cameras to correlate a single lens to a single pixel, preventing overlapping data. The manifold alignment of holes in the 3D print build direction and fine control tripod help align the holes optimally back to the camera. The hole spacing is determined by the test setup and expected field of view with the camera used. This could be developed as a tool to guide users to choose the right spacing between holes so that the output from each does not overlap with the next neighbor setup.

In conjunction with Python analysis software, 1:1 pixel correlation is not required. Overlap in optical emission is still detrimental, but lack of 1:1 correlation provides flexibility in lens grid design to better suit available highspeed camera selections and can aide in manufacturability. Python software provides image of all maximum optical outputs superimposed and labeled by time of occurrence. This image is provided with a graph of ROI (Region of Interest) average pixel intensity versus time. The output is great quick-turnaround feedback for testing.

The inventive concepts taught by way of the examples discussed above are amenable to modification, rearrangement, and embodiment in several ways. Accordingly, although the present disclosure has been described with reference to specific embodiments and examples, persons skilled in the art will recognize that changes may be made in form and detail without departing from the spirit and scope of the disclosure.

What is claimed is:

1. An apparatus for forming an anchor to connect a fiber to an explosive charge wall having an interior wall surface on an interior side and an exterior wall surface on an exterior side, and a fiber insert wall opening through the wall between the interior wall surface and the exterior wall surface, the apparatus comprising:
  an anchor insert tab disposed on the interior side of the wall;
  a top plate disposed on the exterior side of the wall;
  an ST connector disposed on the exterior side of the wall, the ST connector being attached to the top plate to position the ST connector at the fiber insert wall opening for receiving the fiber;
  a plurality of zip ties extending through the anchor insert tab, the wall, and the top plate, the zip ties each having a locking head disposed on the interior side of the wall to press the anchor insert tab against the interior wall surface; and
  a plurality of locking members one for each of the plurality of zip ties, the locking members being disposed on the exterior side of the wall and engaged with the zip ties to press the top plate against the exterior wall surface to form the anchor.

2. The apparatus of claim 1, further comprising:
  a top alignment plate disposed on the exterior side of the wall between the exterior wall surface and the ST connector, the top alignment plate including a bushing configured to extend through the fiber insert wall opening and to receive the ST connector to align the ST connector with the fiber insert wall opening for receiving and aligning the fiber, the plurality of zip ties extending through the anchor insert tab, the wall, the top alignment plate, and the top plate to press the anchor insert tab against the interior wall surface, and the locking members being engaged with the zip ties to press the top plate and the top alignment plate against the exterior wall surface to form the anchor.

3. The apparatus of claim 1, further comprising:
  screws to attach the ST connector to the top plate.

4. The apparatus of claim 1,
  wherein the locking members comprise locking heads of additional zip ties.

5. An explosive charge wall having a plurality of anchors each formed by the apparatus of claim 1, at a plurality of anchor locations on the wall, for connecting a plurality of fibers to the wall.

6. A method of forming an anchor to connect a fiber to an explosive charge wall having an interior wall surface on an interior side and an exterior wall surface on an exterior side, and a fiber insert wall opening through the wall between the interior wall surface and the exterior wall surface at an anchor location for the anchor, the method comprising:
  placing an anchor insert tab on the interior side of the wall over the fiber insert wall opening;
  attaching an ST connector to a top plate;
  placing the top plate on the exterior side of the wall to position the ST connector at the fiber insert wall opening for receiving the fiber;

extending a plurality of zip ties through the anchor insert tab, the wall, and the top plate, the zip ties each having a locking head disposed on the interior side of the wall to press the anchor insert tab against the interior wall surface; and sliding a plurality of locking members on the exterior side of the wall, one for each of the plurality of zip ties, to engage with the zip ties to press the top plate against the exterior wall surface to form the anchor.

7. The method of claim 6, further comprising:
placing a top alignment plate disposed on the exterior side of the wall between the exterior wall surface and the ST connector, the top alignment plate including a bushing configured to extend through the fiber insert wall opening and to receive the ST connector to align the ST connector with the fiber insert wall opening for receiving and aligning the fiber, the plurality of zip ties extending through the anchor insert tab, the wall, the top alignment plate, and the top plate to press the anchor insert tab against the interior wall surface, and the locking members being engaged with the zip ties to press the top plate and the top alignment plate against the exterior wall surface to form the anchor.

8. The method of claim 6, further comprising:
using screws to attach the ST connector to the top plate.

9. The method of claim 6, wherein the interior side of the wall is a fill side of the wall, the method further comprising:
cutting a longitudinal slit in the wall at the anchor location of the fiber insert wall opening; and
inserting the anchor insert tab through the longitudinal slit from the exterior side into the interior side of the wall to be positioned over the fiber insert wall opening on the fill side.

10. The method of claim 6, further comprising:
removing locking heads of additional zip ties to be used as the locking members.

11. The method of claim 6, comprising forming a plurality of anchors at a plurality of anchor locations on the wall, which includes, at each of the plurality of anchor locations:
placing a corresponding anchor insert tab on the interior side of the wall over a corresponding fiber insert wall opening;
attaching a corresponding ST connector to a corresponding top plate;
placing the corresponding top plate on the exterior side of the wall, to position the corresponding ST connector at the corresponding fiber insert wall opening for receiving a corresponding fiber;
extending a plurality of corresponding zip ties each through the corresponding anchor insert tab, the wall, and the corresponding top plate, the corresponding zip ties each having a corresponding locking head disposed on the interior side of the wall to press the corresponding anchor insert tab against the interior wall surface; and
sliding a plurality of corresponding locking members on the exterior side of the wall, one for each of the plurality of the corresponding zip ties, to engage with the corresponding zip ties to press the corresponding top plate against the exterior wall surface.

12. The method of claim 11, further comprising:
forming the plurality of anchors at the plurality of anchor locations on the wall, before connecting the fiber to the ST connector at any of the anchors.

13. The method of claim 12, wherein a plurality of fibers having ST-terminated fiber input ends and fiber output ends are to be connected between the wall to receive the ST-terminated fiber input ends and a fiber panel configured to receive and align the fiber output ends toward a camera, the method further comprising:
presetting the anchor locations on the wall to position the ST-terminated fiber input ends of the plurality of fibers and presetting locations on the fiber panel to position the fiber output ends of the plurality of fibers, before connecting the plurality of fibers between the wall and the fiber panel.

14. The method of claim 13, further comprising:
labeling the plurality of fibers according to the preset anchor locations of the wall for connecting the ST-terminated fiber input ends and the preset locations on the fiber panel for connecting the fiber output ends, before connecting the plurality of fibers between the wall and the fiber panel.

15. An apparatus for forming an anchor to connect a fiber to an explosive charge wall having an interior wall surface on an interior side and an exterior wall surface on an exterior side, and a fiber insert wall opening through the wall between the interior wall surface and the exterior wall surface, the apparatus comprising:
an anchor insert tab disposed on the interior side of the wall;
an ST connector disposed on the exterior side of the wall for receiving the fiber;
a top alignment plate disposed on the exterior side of the wall between the exterior wall surface and the ST connector, the top alignment plate including a bushing configured to extend through the fiber insert wall opening and to receive the ST connector to align the ST connector with the fiber insert wall opening for receiving and aligning the fiber;
a plurality of zip ties extending through the anchor insert tab, the wall, and the top alignment plate, the zip ties each having a locking head disposed on the interior side of the wall to press the anchor insert tab against the interior wall surface; and
a plurality of locking members one for each of the plurality of zip ties, the locking members being disposed on the exterior side of the wall and engaged with the zip ties to press the top alignment plate against the exterior wall surface to form the anchor.

16. The apparatus of claim 15, further comprising:
a top plate disposed on the exterior side of the wall, the ST connector being attached to the top plate to position the ST connector at the fiber insert wall opening for receiving the fiber, the plurality of zip ties extending through the anchor insert tab, the wall, the top alignment plate, and the top plate to press the anchor insert tab against the interior wall surface, and the locking members being engaged with the zip ties to press the top plate and the top alignment plate against the exterior wall surface to form the anchor.

17. The apparatus of claim 16, further comprising:
screws to attach the ST connector to the top plate.

18. The apparatus of claim 15,
wherein the locking members comprise locking heads of additional zip ties.

19. An explosive charge wall having a plurality of anchors each formed by the apparatus of claim 15, at a plurality of anchor locations on the explosive charge wall, for connecting a plurality of fibers to the explosive charge wall at a plurality of fiber insert wall openings.

20. The explosive charge wall of claim 19,
wherein the interior side is a fill side of the explosive charge wall; and wherein the explosive charge wall includes a plurality of longitudinal slits at the plurality of anchor locations at which the plurality of anchors are formed each by inserting the anchor insert tab through a corresponding longitudinal slit from the exterior side into the interior side of the explosive charge wall to be positioned over a corresponding fiber insert wall opening on the fill side.

21. A method for explosive testing, the method comprising:
    connecting fiber output ends of a plurality of fibers to a fiber panel; and
    forming a plurality of anchors at a plurality of anchor locations on an explosive charge wall of an explosive charge to receive fiber input ends of the plurality of fibers, the explosive charge wall having an interior wall surface on an interior side and an exterior wall surface on an exterior side, and a plurality of fiber insert wall openings through the explosive charge wall between the interior wall surface and the exterior wall surface at the plurality of anchor locations for the plurality of anchors;
    forming an anchor of the plurality of anchors comprising:
        placing an anchor insert tab on the interior side of the wall over the fiber insert wall opening;
        attaching an ST connector to a top plate;
        placing the top plate on the exterior side of the wall to position the ST connector at the fiber insert wall opening for receiving the fiber;
        extending a plurality of zip ties through the anchor insert tab, the wall, and the top plate, the zip ties each having a locking head disposed on the interior side of the wall to press the anchor insert tab against the interior wall surface; and
        sliding a plurality of locking members on the exterior side of the wall, one for each of the plurality of zip ties, to engage with the zip ties to press the top plate against the exterior wall surface to form the anchor.

22. The method of claim 21, wherein forming the anchor further comprises:
    placing a top alignment plate disposed on the exterior side of the wall between the exterior wall surface and the ST connector, the top alignment plate including a bushing configured to extend through the fiber insert wall opening and to receive the ST connector to align the ST connector with the fiber insert wall opening for receiving and aligning the fiber, the plurality of zip ties extending through the anchor insert tab, the wall, the top alignment plate, and the top plate to press the anchor insert tab against the interior wall surface, and the locking members being engaged with the zip ties to press the top plate and the top alignment plate against the exterior wall surface to form the anchor.

23. The method of claim 21, wherein the interior side of the wall is a fill side of the wall and wherein forming the anchor further comprises:
    cutting a longitudinal slit in the wall at the anchor location of the fiber insert wall opening for the anchor; and
    inserting the anchor insert tab through the longitudinal slit from the exterior side into the interior side of the wall to be positioned over the fiber insert wall opening on the fill side.

24. The method of claim 21, wherein forming the anchor further comprises:
    removing locking heads of additional zip ties to be used as the locking members.

25. The method of claim 21, wherein forming the anchor further comprises:
    placing a corresponding anchor insert tab on the interior side of the wall over a corresponding fiber insert wall opening;
    attaching a corresponding ST connector to a corresponding top plate;
    placing the corresponding top plate on the exterior side of the wall, to position the corresponding ST connector at the corresponding fiber insert wall opening for receiving a corresponding fiber;
    extending a plurality of corresponding zip ties each through the corresponding anchor insert tab, the wall, and the corresponding top plate, the corresponding zip ties each having a corresponding locking head disposed on the interior side of the wall to press the corresponding anchor insert tab against the interior wall surface; and
    sliding a plurality of corresponding locking members on the exterior side of the wall, one for each of the plurality of the corresponding zip ties, to engage with the corresponding zip ties to press the corresponding top plate against the exterior wall surface.

26. The method of claim 21, wherein the fiber panel is configured to receive and align the fiber output ends toward a camera, the method further comprising:
    presetting the anchor locations on the wall to position the fiber input ends of the plurality of fibers and presetting locations on the fiber panel to position the fiber output ends of the plurality of fibers, before connecting the plurality of fibers between the wall and the fiber panel.

27. The method of claim 26, further comprising:
    labeling the plurality of fibers according to the preset anchor locations on the wall for connecting the fiber input ends and the preset locations on the fiber panel for connecting the fiber output ends, before connecting the plurality of fibers between the wall and the fiber panel.

* * * * *